(12) United States Patent
Auernhammer

(10) Patent No.: US 9,488,288 B2
(45) Date of Patent: Nov. 8, 2016

(54) ACTIVE VALVE FOR DRUG DELIVERY

(75) Inventor: Daniel Auernhammer, Frankfurt am Main (DE)

(73) Assignee: SANOFI-AVENTIS DEUTSCHLAND GMBH, Frankfurt Am Main (DE)

( * ) Notice: Subject to any disclaimer, the term of this patent is extended or adjusted under 35 U.S.C. 154(b) by 0 days.

(21) Appl. No.: 14/114,766

(22) PCT Filed: May 4, 2012

(86) PCT No.: PCT/EP2012/058266
§ 371 (c)(1),
(2), (4) Date: Oct. 30, 2013

(87) PCT Pub. No.: WO2012/152704
PCT Pub. Date: Nov. 15, 2012

(65) Prior Publication Data
US 2014/0066861 A1    Mar. 6, 2014

(30) Foreign Application Priority Data
May 6, 2011   (EP) .................................... 11165129

(51) Int. Cl.
*A61M 5/31*    (2006.01)
*F16K 11/07*   (2006.01)
(Continued)

(52) U.S. Cl.
CPC .............. *F16K 11/0716* (2013.01); *A61M 5/19* (2013.01); *A61M 5/20* (2013.01); *A61M 5/31* (2013.01);
(Continued)

(58) Field of Classification Search
CPC ......... A61M 5/31; A61M 2005/2474; A61M 2005/2496; A61M 2005/3128; A61M 5/19; A61M 5/20; F16K 11/07; F16K 11/0716; Y10T 137/87692

USPC ........ 604/207, 236, 238–239, 244–246, 533, 604/288.03
See application file for complete search history.

(56) References Cited

U.S. PATENT DOCUMENTS 2,289,677 A * 7/1942 Perelson ........................ 215/247
2,342,215 A * 2/1944 Perelson ............... A61J 1/2096
206/219

(Continued)

FOREIGN PATENT DOCUMENTS

JP   H08-503874   4/1996
JP   2001-212235  8/2001
(Continued)

OTHER PUBLICATIONS

International Search Report for Int. App. No. PCT/EP2012/058266, completed Aug. 17, 2012.
(Continued)

*Primary Examiner* — Quynh-Nhu H Vu
(74) *Attorney, Agent, or Firm* — McDonnell Boehnen Hulbert & Berghoff LLP

(57) ABSTRACT

The present invention inter alia relates to a valve arrangement comprising at least two ports, a valve body and a valve piston, wherein the valve piston is at least partially movably arranged in the valve body, wherein the valve arrangement is configured to disable a fluid flow between the at least two ports in a first position of the valve piston in the valve body and to enable the fluid flow in a second position of the valve piston in the valve body, and wherein at least one port of the valve arrangement is arranged in the valve piston and at least one port of the valve arrangement is arranged in the valve body.

12 Claims, 13 Drawing Sheets

(51) Int. Cl.
  *A61M 5/19* (2006.01)
  *A61M 5/20* (2006.01)
  *A61M 5/315* (2006.01)
  *F16K 3/26* (2006.01)
  *A61M 5/24* (2006.01)

(52) U.S. Cl.
  CPC ............ *A61M 5/31546* (2013.01); *F16K 3/26* (2013.01); *A61M 2005/2407* (2013.01); *A61M 2005/2474* (2013.01); *A61M 2005/2496* (2013.01); *A61M 2005/3128* (2013.01); *A61M 2005/31588* (2013.01); *A61M 2205/6036* (2013.01); *Y10T 137/87692* (2015.04)

(56) References Cited

U.S. PATENT DOCUMENTS

| | | | | |
|---|---|---|---|---|
| 2,667,986 | A * | 2/1954 | Perelson | A61J 1/2096 141/19 |
| 3,806,086 | A * | 4/1974 | Cloyd | A61M 39/26 251/149.7 |
| 4,324,239 | A | 4/1982 | Gordon et al. | |
| 4,998,927 | A * | 3/1991 | Vaillancourt | A61M 39/04 604/411 |
| 5,122,123 | A * | 6/1992 | Vaillancourt | A61M 39/14 604/192 |
| 5,147,333 | A * | 9/1992 | Raines | A61M 39/02 137/625.34 |
| 5,360,413 | A * | 11/1994 | Leason et al. | 604/249 |
| 5,533,983 | A * | 7/1996 | Haining | A61M 39/26 251/149.1 |
| 5,772,652 | A * | 6/1998 | Zielinski | A61J 1/2096 215/247 |
| 6,635,043 | B2 * | 10/2003 | Daubert | A61J 1/2096 215/247 |
| 7,867,204 | B2 * | 1/2011 | Bartholomew | A61M 39/02 251/337 |
| 2004/0249235 | A1 | 12/2004 | Connell et al. | |
| 2007/0088313 | A1 | 4/2007 | Zinger et al. | |
| 2011/0230823 | A1 * | 9/2011 | Simonsen | A61M 1/0043 604/30 |

FOREIGN PATENT DOCUMENTS

| | | |
|---|---|---|
| JP | 2003-190279 | 7/2003 |
| WO | 86/01712 | 3/1986 |
| WO | 2007/069907 | 6/2007 |

OTHER PUBLICATIONS

Japanese Office Action for JP App. No. 2014-508828, mailed Feb. 16, 2016.

* cited by examiner

ACTIVE VALVE FOR DRUG DELIVERY

CROSS REFERENCE TO RELATED APPLICATIONS

The present application is a U.S. National Phase Application pursuant to 35 U.S.C. §371 of International Application No. PCT/EP2012/058266 filed May 4, 2012, which claims priority to European Patent Application No. 11165129.5 filed May 6, 2011. The entire disclosure contents of these applications are herewith incorporated by reference into the present application.

FIELD OF DISCLOSURE

The present patent application relates to medical devices of delivering at least two drug agents from separate reservoirs. Such drug agents may comprise a first and a second medicament. The medical device includes a dose setting mechanism for delivering the drug automatically or manually by the user.

The drug agents may be contained in two or more multiple dose reservoirs, containers or packages, each containing independent (single drug compound) or pre-mixed (co-formulated multiple drug compounds) drug agents.

BACKGROUND

Certain disease states require treatment using one or more different medicaments. Some drug compounds need to be delivered in a specific relationship with each other in order to deliver the optimum therapeutic dose. The present patent application is of particular benefit where combination therapy is desirable, but not possible in a single formulation for reasons such as, but not limited to, stability, compromised therapeutic performance and toxicology.

For example, in some cases it might be beneficial to treat a diabetic with a long acting insulin (also may be referred to as the first or primary medicament) along with a glucagon-like peptide-1 such as GLP-1 or GLP-1 analog (also may be referred to as the second drug or secondary medicament).

Accordingly, there exists a need to provide devices for the delivery of two or more medicaments in a single injection or delivery step that is simple for the user to perform without complicated physical manipulations of the drug delivery device. The proposed drug delivery device provides separate storage containers or cartridge retainers for two or more active drug agents. These active drug agents are then only combined and/or delivered to the patient during a single delivery procedure. These active agents may be administered together in a combined dose or alternatively, these active agents may be combined in a sequential manner, one after the other.

SUMMARY

The drug delivery device also allows for the opportunity of varying the quantity of the medicaments. For example, one fluid quantity can be varied by changing the properties of the injection device (e.g., setting a user variable dose or changing the device's "fixed" dose). The second medicament quantity can be changed by manufacturing a variety of secondary drug containing packages with each variant containing a different volume and/or concentration of the second active agent.

The drug delivery device may have a single dispense interface. This interface may be configured for fluid communication with the primary reservoir and with a secondary reservoir of medicament containing at least one drug agent. The drug dispense interface can be a type of outlet that allows the two or more medicaments to exit the system and be delivered to the patient.

The combination of compounds as discrete units or as a mixed unit can be delivered to the body via a double-ended needle assembly. This would provide a combination drug injection system that, from a user's perspective, would be achieved in a manner that closely matches the currently available injection devices that use standard needle assemblies. One possible delivery procedure may involve the following steps:

1. Attach a dispense interface to a distal end of the electro-mechanical injection device. The dispense interface comprises a first and a second proximal needle. The first and second needles pierce a first reservoir containing a primary compound and a second reservoir containing a secondary compound, respectively.

2. Attach a dose dispenser, such as a double-ended needle assembly, to a distal end of the dispense interface. In this manner, a proximal end of the needle assembly is in fluidic communication with both the primary compound and secondary compound.

3. Dial up/set a desired dose of the primary compound from the injection device, for example, via a graphical user interface (GUI).

4. After the user sets the dose of the primary compound, the micro-processor controlled control unit may determine or compute a dose of the secondary compound and preferably may determine or compute this second dose based on a previously stored therapeutic dose profile. It is this computed combination of medicaments that will then be injected by the user. The therapeutic dose profile may be user selectable.

5. Optionally, after the second dose has been computed, the device may be placed in an armed condition. In such an optional armed condition, this may be achieved by pressing and/or holding an "OK" button on a control panel. This condition may provide for greater than a predefined period of time before the device can be used to dispense the combined dose.

6. Then, the user will insert or apply the distal end of the dose dispenser (e.g., a double ended needle assembly) into the desired injection site. The dose of the combination of the primary compound and the secondary compound (and potentially a third medicament) is administered by activating an injection user interface (e.g., an injection button).

Both medicaments may be delivered via one injection needle or dose dispenser and in one injection step. This offers a convenient benefit to the user in terms of reduced user steps compared to administering two separate injections.

To prevent cross contamination and back flow of the first and second medicaments contained in the first and second reservoirs, respectively, the dispense interface may comprise a valve arrangement.

Preferably valves with a low opening pressure threshold, minimal resistance to flow when open and an effective seal against back pressure are used in this valve arrangement. Furthermore, preferably simply mountable valves are used in this valve arrangement.

However, only difficulty mountable valve arrangements and/or passive valve arrangements with a rather high opening pressure threshold, high resistance to flow when open and/or an less effective seal against back pressure are used in such valve arrangements in the prior art.

Therefore, the present invention inter-alia faces the technical problem of providing a simply mountable valve arrangement, for instance a valve arrangement for a dispense interface.

According to the present invention, a valve arrangement comprises at least two ports, a valve body and a valve piston, wherein the valve piston is at least partially movably arrangable or arranged in the valve body, wherein the valve arrangement is configured to disable a fluid flow between the at least two ports in a first position of the valve piston in the valve body and to enable the fluid flow in a second position of the valve piston in the valve body, and wherein at least one port of the valve arrangement is arranged in the valve piston and at least one port of the valve arrangement is arranged in the valve body. In an example embodiment, said first and second position are a first and a second longitudinal position of said valve piston in said valve body. Thus, the valve piston may move in a longitudinal direction in the valve body.

According to the present invention, an apparatus comprises the valve arrangement, wherein the apparatus is a medical device configured to eject a medicament or a dispense interface attachable to a medical device configured to eject a medicament.

According to the present invention, a method comprises moving a fluid reservoir connected to the at least one port arranged in the valve piston of the valve arrangement of the apparatus according to the present invention relatively to the apparatus, and enabling a fluid flow between the at least two ports of the valve arrangement of the apparatus, wherein the moving of the fluid reservoir causes moving the valve piston from the first position in the valve body to the second position in the valve body.

The apparatus may be a drug delivery device such as a medical device configured to eject a drug agent (e.g. a dose of a medicament) such as an infusion device or an injection device, for instance an insulin injection pen. Injection devices may be used either by medical personnel or by patients themselves. As an example, type-1 and type-2 diabetes may be treated by patients themselves by injection of insulin doses, for example once or several times per day.

For instance, the apparatus is a medical device configured to eject at least two drug agents from separate reservoirs (e.g. cartridges) comprising a first and a second medicament, respectively, but it is not limited thereto. Alternatively, the medical device is for instance a conventional medical device configured to eject a drug agent from a single reservoir (e.g. a single cartridge) such as Applicant's Solostar insulin injection pen.

Alternatively, the apparatus may be a (disposable) part attachable to a medical device such as a drug delivery device. For instance, the apparatus is a dispense interface attachable to a medical device configured to eject a drug agent. A dispense interface may be configured to be in fluid communication with at least one fluid reservoir (e.g. one cartridge) of the medical device containing at least one medicament. For instance, the dispense interface is a type of outlet that allows the at least one medicament to exit the medical device.

The valve arrangement comprises at least two ports, a valve piston and a valve body.

The at least two ports of the valve arrangement may be an inlet port and an outlet port. The inlet port may be arranged in the valve piston. In particular, the inlet port may at least partially be arranged in a base of the valve piston. The inlet port may be configured to reside in fluid connection with a fluid reservoir of the apparatus and/or the valve arrangement. The fluid reservoir is for instance a replaceable cartridge and/or a refillable container, for instance containing a medicament.

As an example, the inlet port may be formed from a canula (longitudinally) arranged in the valve piston. At least a first end of the canula may protrude over a base of the valve piston and may be configured to pierce a septum of the fluid reservoir such that the inlet port is connected to the fluid reservoir and resides in fluid communication with the fluid reservoir. In this example, when the inlet port is connected to the fluid reservoir, a friction fit between the valve piston and the reservoir, in particular between the septum and the first end of the canula, is formed.

The valve body may be formed from an opening (e.g. a blind hole) configured to at least partially receive the valve piston. For instance, a cross-section of the inlet of the valve body corresponds to a cross-section of the valve-piston such that the lateral surface at the inlet of the valve body is configured to tightly encompass a lateral surface of the valve piston, when the valve piston is at least partially, longitudinally received in the opening. For instance, the valve piston is only longitudinally movable in the valve body. When the valve piston is received in the valve body, the longitudinal axis of the valve body, for instance the longitudinal axis of the opening, may correspond to the longitudinal axis of the valve piston.

At the base of the opening, a recess may be arranged in the lateral surface such that the valve piston and the valve body form a cavity, when the valve piston is received in the valve body. Alternatively or additionally, at the base of the opening, a mechanical stop protruding over the base of the opening may be arranged to prevent the valve piston touching the base of the opening. Alternatively or additionally, the mechanical stop may be a projection arranged at the lateral surface of the recess. The mechanical stop may lower the diameter of the opening. For instance, the mechanical stop prevents a protruding end of the canula arranged in the valve piston to touch the base of the recess, when the valve piston is received in the valve body.

The outlet port may be arranged in the lateral surface of the opening such that the lateral surface of the valve piston may seal the outlet port in a first longitudinal position in the valve body and may unseal the outlet port in a second longitudinal position in the valve body. In particular, the first and second longitudinal position may be the first and second position of the valve piston in the valve body such that a fluid flow between the at least two ports is disabled in the first longitudinal position and enabled in the second longitudinal position. For instance, a recess is arranged in the lateral surface of the valve piston, wherein the recess unseals the outlet port, when the recess is aligned with the outlet port.

When a fluid reservoir is connected to the inlet port arranged in the valve piston and the valve piston is at least partially received in the valve body, moving the reservoir relatively to the valve body may cause the valve piston to be correspondingly moved in the valve body. In particular, longitudinally moving the fluid reservoir relatively to the valve body may cause the valve piston to be also longitudinally moved relatively to and/or in the valve body. For instance, longitudinally moving the fluid reservoir towards the valve body may cause the valve piston to be moved (e.g. the valve piston is pushed) from the first longitudinal position to the second longitudinal position and thereby enabling a fluid flow between the at least two ports of the valve arrangement. Moving the fluid reservoir in the opposite direction may accordingly cause the valve piston to be moved (e.g. the valve piston is pulled) from the second longitudinal position to the first longitudinal position and thereby disabling a fluid flow between the at least two ports of the valve arrangement.

The first position may be the initial position of the valve piston in the valve body.

For instance, when the valve piston is in the first longitudinal position in the valve body and the inlet arranged in the valve piston is connected to a cartridge containing a medicament of a medical device configured to eject a medicament and a bung of the cartridge is pressed (e.g. moved towards the valve body) in order to build up pressure in the cartridge and to initiate an ejection, the cartridge may be moved because of the friction between the bung and the cartridge. The movement of the cartridge may then cause a corresponding movement of the valve piston in the valve body from the first position to the second position. In the second position, the valve piston may reside on a mechanical stop at the base of the valve body such that a further moving of the valve piston in the valve body is prevented. In the second position, the valve arrangement is open and, due to the build up pressure in the cartridge, a fluid flow from the cartridge to the outlet port of the valve body may be initiated such that the medicament may exit the medical device at an outlet arranged at the outlet port of the valve body.

For instance, if the cartridge and/or the valve piston is for instance spring-loaded and the pressure on the bung of the cartridge is released, the cartridge may be moved in the opposite direction and the valve piston may be moved from the second position to the first position. In the first position, the valve is closed and a back-flow of the medicament into the cartridge is prevented. This is inter-alia advantageous to prevent a contamination of the medicament contained in the cartridge.

As an example, the valve piston (e.g. a plunger) is inserted into the opening of the valve body (e.g. a hole). The first position is defined by the uncompressed state of a spring surrounding the valve piston. Then the cartridge may be applied. By pressing on the bung of the cartridge, a fluidic flow may be initiated, filling the fluidic system and compressing the spring. The valve may be in an open state now. For instance, by releasing the pressure on the bung and allowing the cartridge to move backwards, the valve piston may be lifted. Then the recess (e.g. a channel) arranged on the lateral surface of the valve piston may be no longer aligned with the outlet port, preventing a fluidic flow. The system may be in a close state now.

The present invention provides a valve arrangement formed from at least two pieces, the valve body and the valve piston, wherein the valve piston may be received in the valve body, when the valve arrangement is to be connected to a fluid reservoir. This is inter-alia advantageous in order to provide a simply mountable valve arrangement, for instance a valve arrangement for a dispense interface.

Furthermore, the present invention provides an active valve arrangement, wherein the valve arrangement is actively opened and closed depending on a movement of a fluid reservoir and/or a valve piston. This is inter alia advantageous in order to provide a valve without an opening pressure threshold, minimal resistance to flow when open and/or an effective seal against back pressure.

In the following, features and embodiments (exhibiting further features) of the present invention will be described, which are understood to equally apply to the apparatus, the valve arrangement and the method as described above. These single features/embodiments are considered to be exemplary and non-limiting, and to be respectively combinable independently from other disclosed features/embodiments of the apparatus, the valve arrangement and the method as described above. Nevertheless, these features/embodiments shall also be considered to be disclosed in all possible combinations with each other and with the apparatus, the valve arrangement and the method as described above. For instance, a mentioning that an apparatus and/or a valve arrangement according to the present invention is configured to perform a certain action should be understood to also disclose an according method step of the method according to the present invention.

According to an embodiment of the present invention, the valve body comprises an opening configured to at least partially receive the valve piston and to form a cavity with the valve piston. For instance, an inlet of the opening is configured to laterally, tightly encompass the valve piston. The valve cavity may in one direction be defined by the base of the valve body and a base of the valve piston and in another direction by the lateral surface of the valve body and the valve piston.

This is inter-alia advantageous in order to seal the valve cavity and/or the outlet port by the valve piston.

According to an embodiment of the present invention, the valve body is formed from at least a cover part and a base part, the cover part configured to form an inlet of the opening and the base part configured to form the cavity with the valve piston. The outlet port may be sandwiched (i.e. arranged) between the base part and the cover part.

For instance, the cover part is formed from a cover plate and the base part is formed from a cover plate. The cover plate may feature an opening in the lateral dimension of the valve piston to provide sealing when inserted. A fluidic channel as outlet port is arranged in a surface of the cover plate oriented towards the base plate. The fluidic channel may end in an outlet of the valve arrangement and/or the apparatus. The surface of the cover plate oriented towards the base plate may be inclined at the opening. For instance, the cover plate is thickest at the fluidic channel.

The base plate may feature a recess (e.g. a cylindrical recess) of a selected depth to provide space for the valve piston to travel between the first and second position in the valve body. The diameter of the recess may be greater than the diameter of the opening of the cover plate. For instance, the second position of the valve piston in the valve body is defined by a mechanical stop (e.g. a projection arranged at the lateral surface of the recess) to assure a remaining gap between the valve piston, in particular the inlet port arranged in the valve piston, and the base of the recess. The surface of the base plate oriented towards the cover plate may be inclined at the cylindrical recess. In particular, the inclination of the base plate may correspond to the inclination of the cover plate.

The valve body may be formed by bonding the surface of the cover plate oriented towards the base plate and the surface of the base plate oriented towards the cover plate, for instance by adhesive bonding, welding or the like. For instance, the lateral surface of the opening of the cover plate and the lateral surface of the recess of the base plate are aligned at the outlet port.

The base plate may be configured to inter-alia form a cavity with the valve piston opposite to the outlet port and/or at the base of the recess.

This embodiment is inter-alia advantageous in order to effectuate the fluidic control mechanism of the valve arrangement by providing or inhibiting access to the outlet port, for instance via a recess arranged in the lateral surface of the valve piston. Furthermore, this embodiment is inter-alia advantageous in order to simplify mounting the valve body.

According to an embodiment of the present invention, the cavity is (longitudinally) variable depending on the positions of the valve piston in the valve body (the position being longitudinally different positions). For instance, the valve cavity is defined by the valve body and the valve piston. As described above, the valve cavity may be defined by bases of the valve body and the valve piston and/or by lateral surfaces of the valve body and the valve piston. The valve cavity may be larger in the first position of the valve piston in the valve body and smaller in the second position of the valve piston in the valve body. Alternatively, the valve cavity may be smaller in the first position of the valve piston in the valve body and larger in the second position of the valve piston in the valve body.

According to an embodiment of the present invention, the at least one port arranged in the valve piston ends in the cavity and, when the valve piston is in the second position in the valve body, the at least one port arranged in the valve body ends in the cavity. When the at least two ports end in the valve cavity, a fluid flow between the at least two ports is enabled and, otherwise, a fluid flow is disabled. This embodiment is inter-alia advantageous in order to actively control the fluid flow between the at least two ports of the valve arrangement by moving the valve piston.

According to an embodiment of the present invention, a lateral surface of the valve piston is configured to seal the at least one port arranged in the valve body in the first position in the valve body and to unseal the at least one port arranged in the valve body in the second position in the valve body. This embodiment is inter-alia advantageous in order to actively control the fluid flow between the at least two ports of the valve arrangement by moving the valve piston. For instance, the lateral surface of the valve piston may substantially correspond to the lateral surface of the valve piston at the at least one port arranged in the valve body such that the lateral surface of the valve piston covers the at least one port arranged in the valve body in the first position of the valve piston in the valve body. However, in the second position of the valve piston in the valve body, the lateral surface of the valve piston may not cover the at least one port arranged in the valve body.

This embodiment is inter-alia advantageous in order to actively control the fluid between the at least two ports of the valve arrangement by moving the valve piston.

According to an embodiment of the present invention, a lateral surface of the valve piston comprises a recess. For instance, the recess is arranged in the lateral surface of the valve piston such that, in the second position of the valve piston in the valve body, the recess is aligned with the at least one port arranged in the valve body. However, in the first position of the valve piston in the valve body, the recess is not aligned with the at least one port arranged in the valve body.

The recess may at least partially be circularly, helix-likely and/or longitudinally arranged in the lateral surface of the valve piston. The recess may end in the valve cavity. For instance, the recess may be an engraved channel in the lateral surface of the valve piston. The recess may unseal the at least one port arranged in the valve body in the second position of the valve piston in the valve body.

This embodiment is inter-alia advantageous in order to actively control the fluid between the at least two ports of the valve arrangement by moving the valve piston, for instance by aligning the recess to the at least one port arranged in the valve body.

According to an embodiment of the present invention, the recess is not in fluid communication with the at least one port in the valve body in the first position, wherein the recess is in fluid communication with the at least one port in the valve body in the second position.

This embodiment is inter-alia advantageous in order to actively control the fluid between the at least two ports of the valve arrangement by moving the valve piston, for instance by aligning the recess to the at least one port arranged in the valve body.

According to an embodiment of the present invention, the valve piston is substantially cylindrical.

According to an embodiment of the present invention, the valve piston is spring-loaded. For instance, the valve piston is spring-loaded in the first and/or second position in the valve body. Alternatively or additionally, a cartridge of a medical device may be spring-loaded, when connected to the valve piston. For instance, a spring surrounds an end of the valve piston. For instance the spring is arranged between a rim of the valve piston and the valve body, when the valve piston is at least partially received in the valve body. Alternatively or additionally, the spring may be arranged between a base of the valve piston oriented towards the base of the valve body and the base of the valve body, when the valve piston is received in the valve body.

In an uncompressed state of the spring the valve piston may be in the first position in the valve body disabling the fluid flow. In a compressed state the valve piston may be in the second position in the valve body enabling the fluid flow. Accordingly, in the second position of the valve piston in the valve body the spring causes an elastic counterforce moving the valve piston to the first position in the valve body. The valve piston may only be in the second position, when a force at least outweighing the elastic counterforce is applied on the valve piston. When the force outweighing the elastic counterforce is released, the valve piston may be moved to the first position. The spring may secure the valve piston in the first position.

As described above, a pressure on a bung of a cartridge connected to the valve piston may cause a force outweighing the elastic counterforce such that the valve piston is moved from the first to the second position. However, when the pressure is released, the valve piston may be moved to the first position.

This embodiment is inter-alia advantageous to prevent a backflow of a fluid and/or to secure the valve piston in the first position.

According to an embodiment of the present invention, the at least one port arranged in the valve piston is formed from a through opening in the valve piston. For instance, the through opening is arranged along the longitudinal axis of the valve piston. The through opening may penetrate the valve piston from one base to the opposite base of the valve piston, for instance from a top base to a bottom base.

The through opening may be connected with a fluid connector configured to connect the at least one port arranged in the valve piston with a fluid reservoir, such as a luer-connector, a canula or the like. The connection between the inlet port and the fluid reservoir may also form a connection between the valve piston and the fluid reservoir.

This embodiment is inter-alia advantageous to allow moving the valve piston (e.g. pushing and pulling) in the valve body by moving the fluid reservoir connected to the valve piston.

According to an embodiment of the present invention, the through opening in the valve piston is formed from a canula, wherein one end of the canula is configured to pierce a septum of a fluid reservoir such that the at least one port arranged in the valve piston resides in fluid communication with the fluid reservoir.

As described above, at least a first end of the canula may protrude over a base of the valve piston and may be configured to pierce a septum of a fluid reservoir such that the inlet port is connected to the fluid reservoir and resides in fluid communication with the fluid reservoir. When the inlet port is connected to the fluid reservoir, a friction fit between the valve piston and the reservoir, in particular between the septum and the first end of the canula, is formed. The friction between the septum and the canula may be higher than the friction between the valve piston and the valve body.

A second end of the canula may end at an opposite base of the valve piston. For instance, the second end of the canula may be configured to end in the valve cavity, when the valve piston is at least partially received in the valve body.

The valve piston may be configured to be moved (e.g. pushed and pulled) in the valve body by moving the fluid reservoir, when the valve piston is connected to the fluid reservoir.

As described above, for instance, applying pressure on a bung of the fluid reservoir in order to build up pressure therein may cause the reservoir to be moved because of the friction between the bung and the fluid reservoir. The movement of the fluid reservoir may then cause a corresponding movement of the valve piston in the valve body. For instance, the valve piston is moved from the first position in the valve body to the second position in the valve body enabling a fluid flow from the fluid reservoir via the at least one port arranged in the valve piston and the valve cavity to the at least one port arranged in the valve body.

This embodiment is inter-alia advantageous in order to actively control the fluid flow between the at least two ports of the valve arrangement by moving a fluid reservoir.

According to an embodiment of the present invention, the valve piston is spring-loaded such that moving the fluid reservoir relatively to the apparatus is against the spring-load and causes an elastic counterforce. As described above, this embodiment is inter-alia advantageous to prevent a backflow of a fluid and/or to secure the valve piston in the first position.

DETAILED DESCRIPTION

Figure 1:
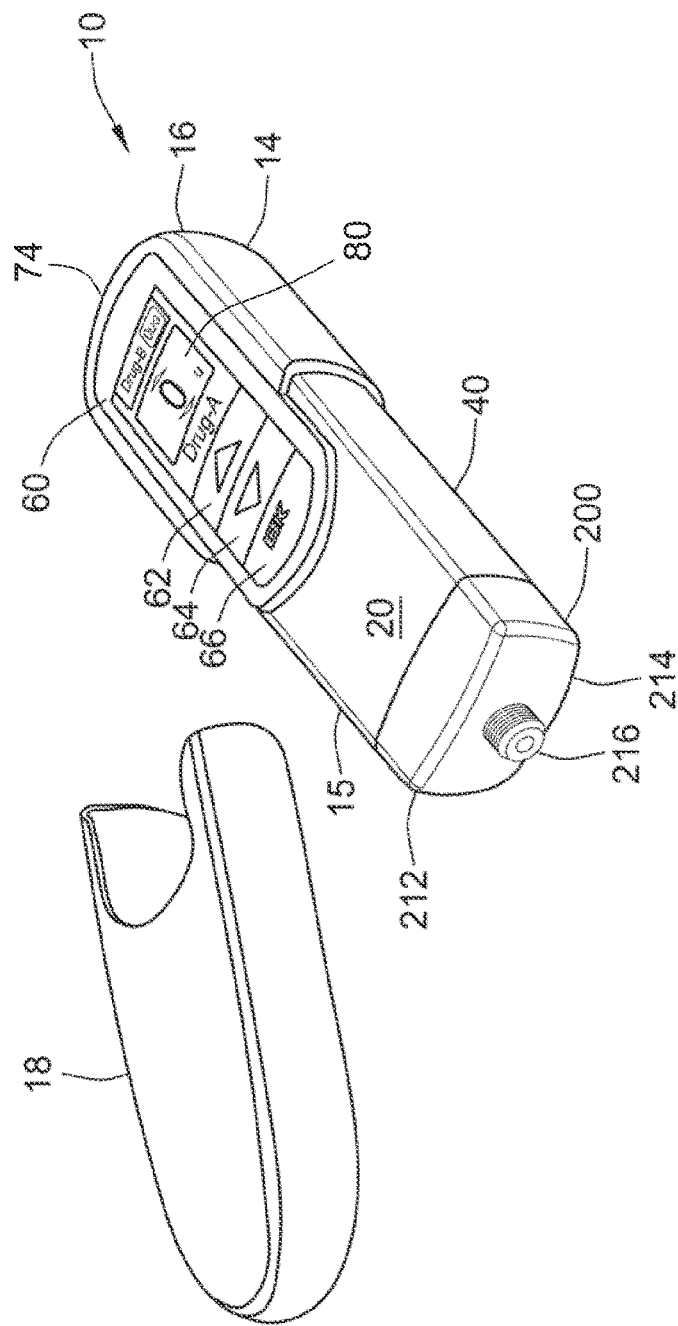
FIG. 1 illustrates a perspective view of the delivery device illustrated in FIG. 1a and 1b with an end cap of the device removed.
Figure 2:
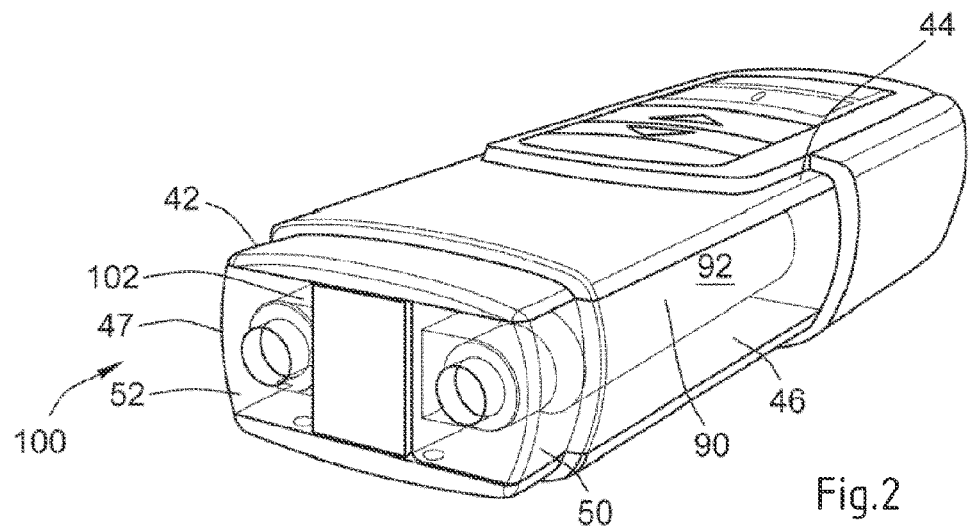
FIG. 2 illustrates a perspective view of the delivery device distal end showing the cartridge.

The drug delivery device illustrated in FIG. 1 comprises a main body 14 that extends from a proximal end 16 to a distal end 15. At the distal end 15, a removable end cap or cover 18 is provided. This end cap 18 and the distal end 15 of the main body 14 work together to provide a snap fit or form fit connection so that once the cover 18 is slid onto the distal end 15 of the main body 14, this frictional fit between the cap and the main body outer surface 20 prevents the cover from inadvertently falling off the main body.

The main body 14 contains a micro-processor control unit, an electro-mechanical drive train, and at least two medicament reservoirs. When the end cap or cover 18 is removed from the device 10 (as illustrated in FIG. 1), a dispense interface 200 is mounted to the distal end 15 of the main body 14, and a dose dispenser (e.g., a needle assembly) is attached to the interface. The drug delivery device 10 can be used to administer a computed dose of a second medicament (secondary drug compound) and a variable dose of a first medicament (primary drug compound) through a single needle assembly, such as a double ended needle assembly.

A control panel region 60 is provided near the proximal end of the main body 14. Preferably, this control panel region 60 comprises a digital display 80 along with a plurality of human interface elements that can be manipulated by a user to set and inject a combined dose. In this arrangement, the control panel region comprises a first dose setting button 62, a second dose setting button 64 and a third button 66 designated with the symbol "OK." In addition, along the most proximal end of the main body, an injection button 74 is also provided (not visible in the perspective view of FIG. 1).

The cartridge holder 40 can be removably attached to the main body 14 and may contain at least two cartridge retainers 50 and 52. Each retainer is configured so as to contain one medicament reservoir, such as a glass cartridge. Preferably, each cartridge contains a different medicament.

In addition, at the distal end of the cartridge holder 40, the drug delivery device illustrated in FIG. 1 includes a dispense interface 200. As will be described in relation to FIG. 4, in one arrangement, this dispense interface 200 includes a main outer body 212 that is removably attached to a distal end 42 of the cartridge housing 40. As can be seen in FIG. 1, a distal end 214 of the dispense interface 200 preferably comprises a needle hub 216. This needle hub 216 may be configured so as to allow a dose dispenser, such as a conventional pen type injection needle assembly, to be removably mounted to the drug delivery device 10.

Once the device is turned on, the digital display 80 shown in FIG. 1 illuminates and provides the user certain device information, preferably information relating to the medicaments contained within the cartridge holder 40. For example, the user is provided with certain information relating to both the primary medicament (Drug A) and the secondary medicament (Drug B).

Figure 3:
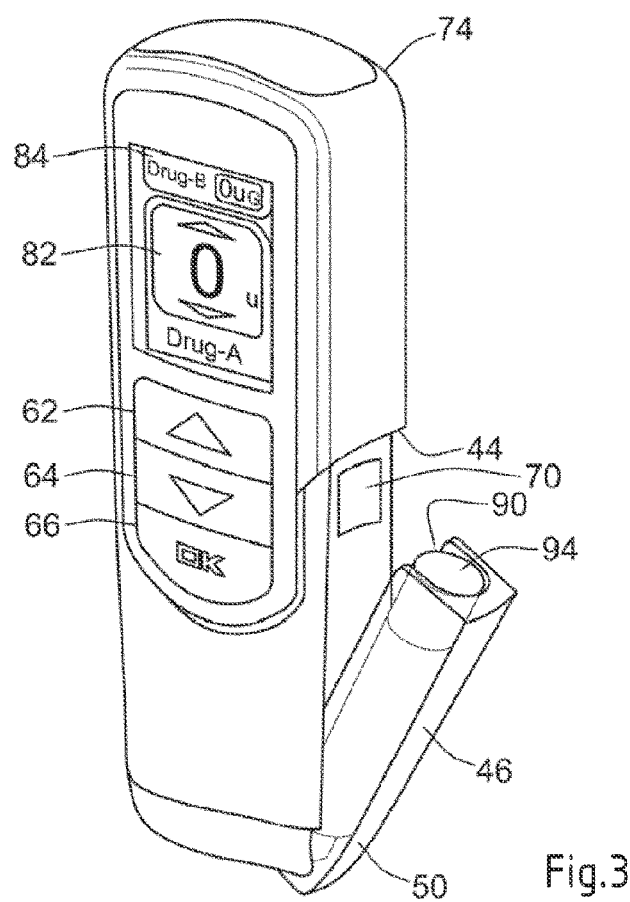
FIG. 3 illustrates a perspective view of the cartridge holder illustrated in FIG. 1 with one cartridge retainer in an open position.

As shown in FIG. 3, the first and a second cartridge retainers 50, 52 comprise hinged cartridge retainers. These hinged retainers allow user access to the cartridges. FIG. 3 illustrates a perspective view of the cartridge holder 40 illustrated in FIG. 1 with the first hinged cartridge retainer 50 in an open position. FIG. 3 illustrates how a user might access the first cartridge 90 by opening up the first retainer 50 and thereby having access to the first cartridge 90.

Figure 4:
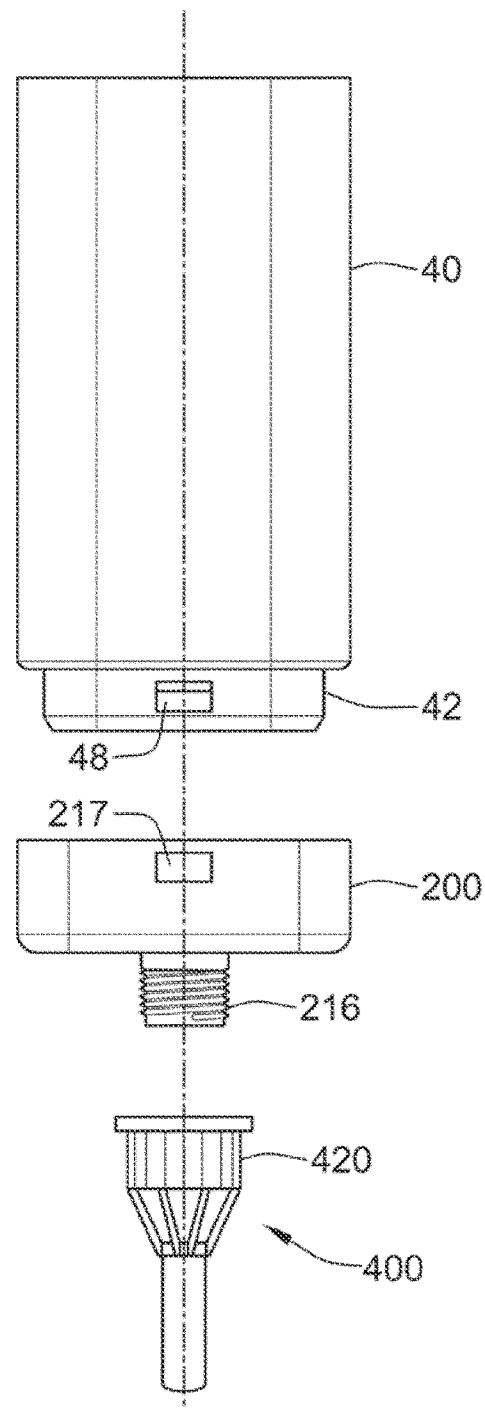
FIG. 4 illustrates a dispense interface and a dose dispenser that may be removably mounted on a distal end of the delivery device illustrated in FIG. 1.

As mentioned above when discussing FIG. 1, a dispense interface 200 is coupled to the distal end of the cartridge holder 40. FIG. 4 illustrates a flat view of the dispense interface 200 unconnected to the distal end of the cartridge holder 40. A dose dispenser or needle assembly that may be used with the interface 200 is also illustrated and is provided in a protective outer cap 420.

Figure 5:
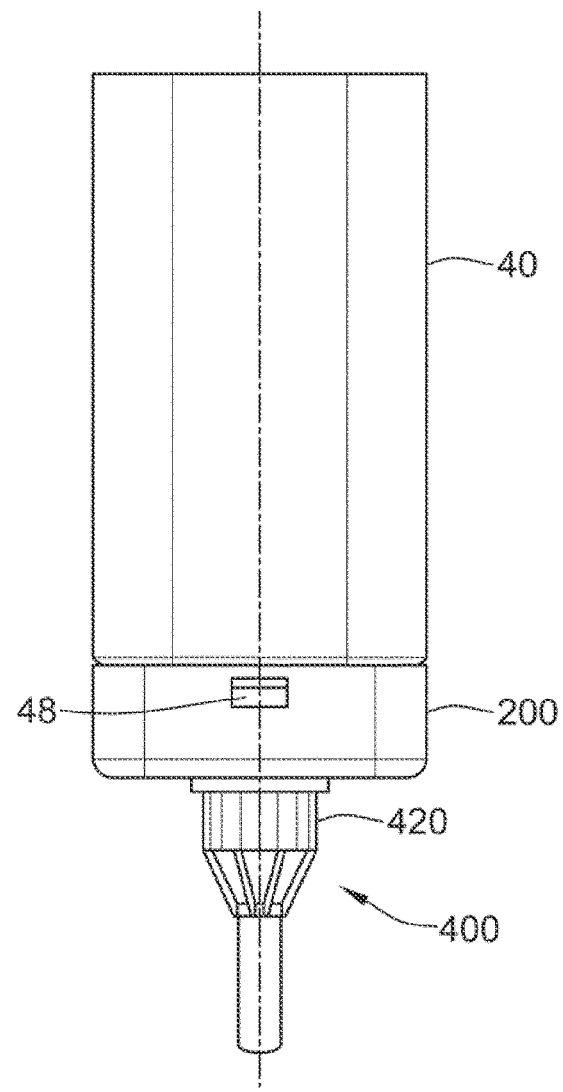
FIG. 5 illustrates the dispense interface and the dose dispenser illustrated in FIG. 4 mounted on a distal end of the delivery device illustrated in FIG. 1.

In FIG. 5, the dispense interface 200 illustrated in FIG. 4 is shown coupled to the cartridge holder 40. The axial attachment means between the dispense interface 200 and the cartridge holder 40 can be any known axial attachment means to those skilled in the art, including snap locks, snap fits, snap rings, keyed slots, and combinations of such connections. The connection or attachment between the dispense interface and the cartridge holder may also contain additional features (not shown), such as connectors, stops, splines, ribs, grooves, pips, clips and the like design features, that ensure that specific hubs are attachable only to matching drug delivery devices. Such additional features would prevent the insertion of a non-appropriate secondary cartridge to a non-matching injection device.

Figure 6:
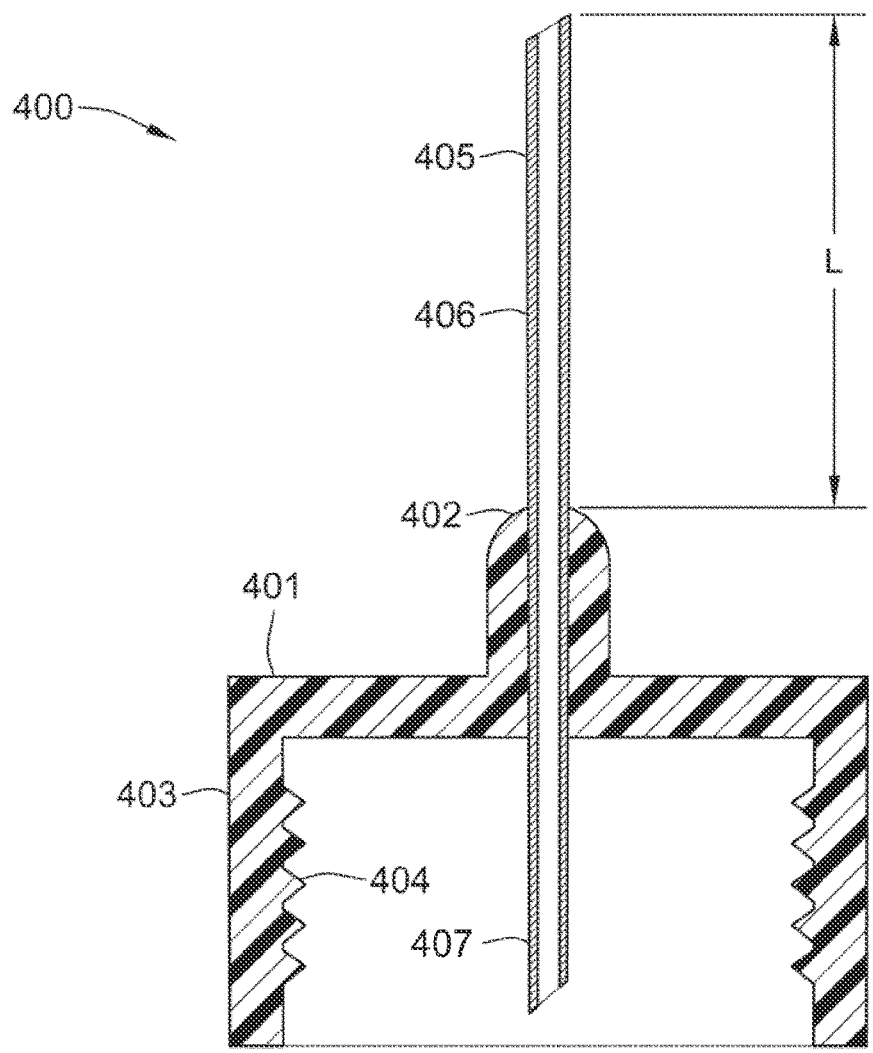
FIG. 6 illustrates one arrangement of the dose dispenser that may be mounted on a distal end of the delivery device.
Figure 7:
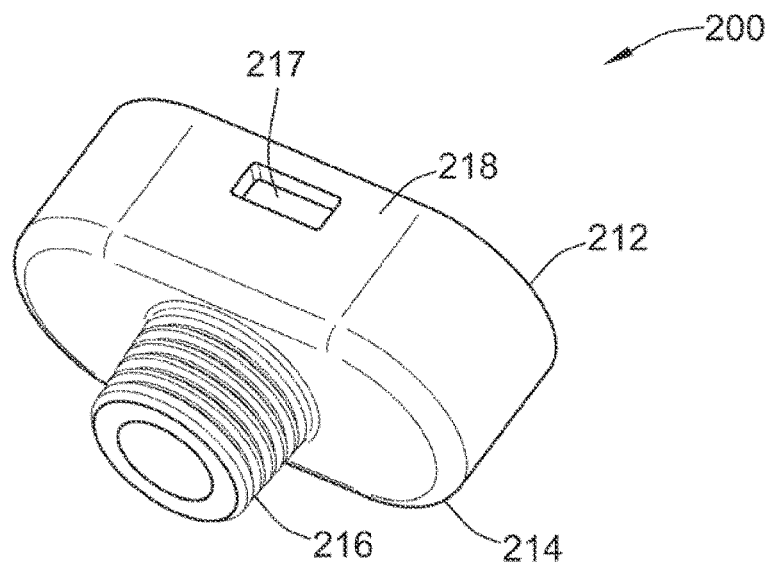
FIG. 7 illustrates a perspective view of the dispense interface illustrated in FIG. 4.

FIG. 5 also illustrates the needle assembly 400 and protective cover 420 coupled to the distal end of the dispense interface 200 that may be screwed onto the needle hub of the interface 200. FIG. 6 illustrates a cross sectional view of the double ended needle assembly 402 mounted on the dispense interface 200 in FIG. 5.

The needle assembly 400 illustrated in FIG. 6 comprises a double ended needle 406 and a hub 401. The double ended needle or cannula 406 is fixedly mounted in a needle hub 401. This needle hub 401 comprises a circular disk shaped element which has along its periphery a circumferential depending sleeve 403. Along an inner wall of this hub member 401, a thread 404 is provided. This thread 404 allows the needle hub 401 to be screwed onto the dispense interface 200 which, in one preferred arrangement, is provided with a corresponding outer thread along a distal hub. At a center portion of the hub element 401 there is provided a protrusion 402. This protrusion 402 projects from the hub in an opposite direction of the sleeve member. A double ended needle 406 is mounted centrally through the protrusion 402 and the needle hub 401. This double ended needle 406 is mounted such that a first or distal piercing end 405 of the double ended needle forms an injecting part for piercing an injection site (e.g., the skin of a user).

Similarly, a second or proximal piercing end 406 of the needle assembly 400 protrudes from an opposite side of the circular disc so that it is concentrically surrounded by the sleeve 403. In one needle assembly arrangement, the second or proximal piercing end 406 may be shorter than the sleeve 403 so that this sleeve to some extent protects the pointed end of the back sleeve. The needle cover cap 420 illustrated in FIGS. 4 and 5 provides a form fit around the outer surface 403 of the hub 401.

Referring now to FIGS. 4 to 11, one preferred arrangement of this interface 200 will now be discussed. In this one preferred arrangement, this interface 200 comprises:

a. a main outer body 210,
b. an first inner body 220,
c. a second inner body 230,
d. a first piercing needle 240,
e. a second piercing needle 250,
f. a valve seal 260, and
g. a septum 270.

The main outer body 210 comprises a main body proximal end 212 and a main body distal end 214. At the proximal end 212 of the outer body 210, a connecting member is configured so as to allow the dispense interface 200 to be attached to the distal end of the cartridge holder 40. Preferably, the connecting member is configured so as to allow the dispense interface 200 to be removably connected the cartridge holder 40. In one preferred interface arrangement, the proximal end of the interface 200 is configured with an upwardly extending wall 218 having at least one recess. For example, as may be seen from FIG. 8, the upwardly extending wall 218 comprises at least a first recess 217 and a second recess 219.

Preferably, the first and the second recesses 217, 219 are positioned within this main outer body wall so as to cooperate with an outwardly protruding member located near the distal end of the cartridge housing 40 of the drug delivery device 10. For example, this outwardly protruding member 48 of the cartridge housing may be seen in FIGS. 4 and 5. A second similar protruding member is provided on the opposite side of the cartridge housing. As such, when the interface 200 is axially slid over the distal end of the cartridge housing 40, the outwardly protruding members will cooperate with the first and second recess 217, 219 to form an interference fit, form fit, or snap lock. Alternatively, and as those of skill in the art will recognize, any other similar connection mechanism that allows for the dispense interface and the cartridge housing 40 to be axially coupled could be used as well.

The main outer body 210 and the distal end of the cartridge holder 40 act to form an axially engaging snap lock or snap fit arrangement that could be axially slid onto the distal end of the cartridge housing. In one alternative arrangement, the dispense interface 200 may be provided with a coding feature so as to prevent inadvertent dispense interface cross use. That is, the inner body of the hub could be geometrically configured so as to prevent an inadvertent cross use of one or more dispense interfaces.

A mounting hub is provided at a distal end of the main outer body 210 of the dispense interface 200. Such a mounting hub can be configured to be releasably connected to a needle assembly. As just one example, this connecting means 216 may comprise an outer thread that engages an inner thread provided along an inner wall surface of a needle hub of a needle assembly, such as the needle assembly 400 illustrated in FIG. 6. Alternative releasable connectors may also be provided such as a snap lock, a snap lock released through threads, a bayonet lock, a form fit, or other similar connection arrangements.

The dispense interface 200 further comprises a first inner body 220. Certain details of this inner body are illustrated in FIG. 8-11. Preferably, this first inner body 220 is coupled to an inner surface 215 of the extending wall 218 of the main outer body 210. More preferably, this first inner body 220 is coupled by way of a rib and groove form fit arrangement to an inner surface of the outer body 210. For example, as can be seen from FIG. 9, the extending wall 218 of the main outer body 210 is provided with a first rib 213*a* and a second rib 213*b*. This first rib 213*a* is also illustrated in FIG. 10. These ribs 213*a* and 213*b* are positioned along the inner surface 215 of the wall 218 of the outer body 210 and create a form fit or snap lock engagement with cooperating grooves 224*a* and 224*b* of the first inner body 220. In a preferred arrangement, these cooperating grooves 224*a* and 224*b* are provided along an outer surface 222 of the first inner body 220.

Figure 8:
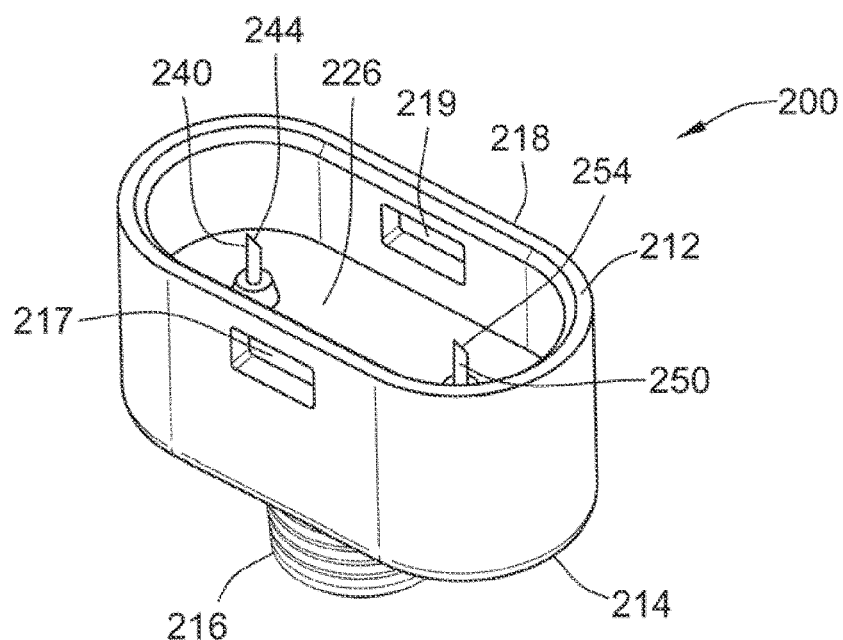
FIG. 8 illustrates another perspective view of the dispense interface illustrated in FIG. 4.
Figure 9:
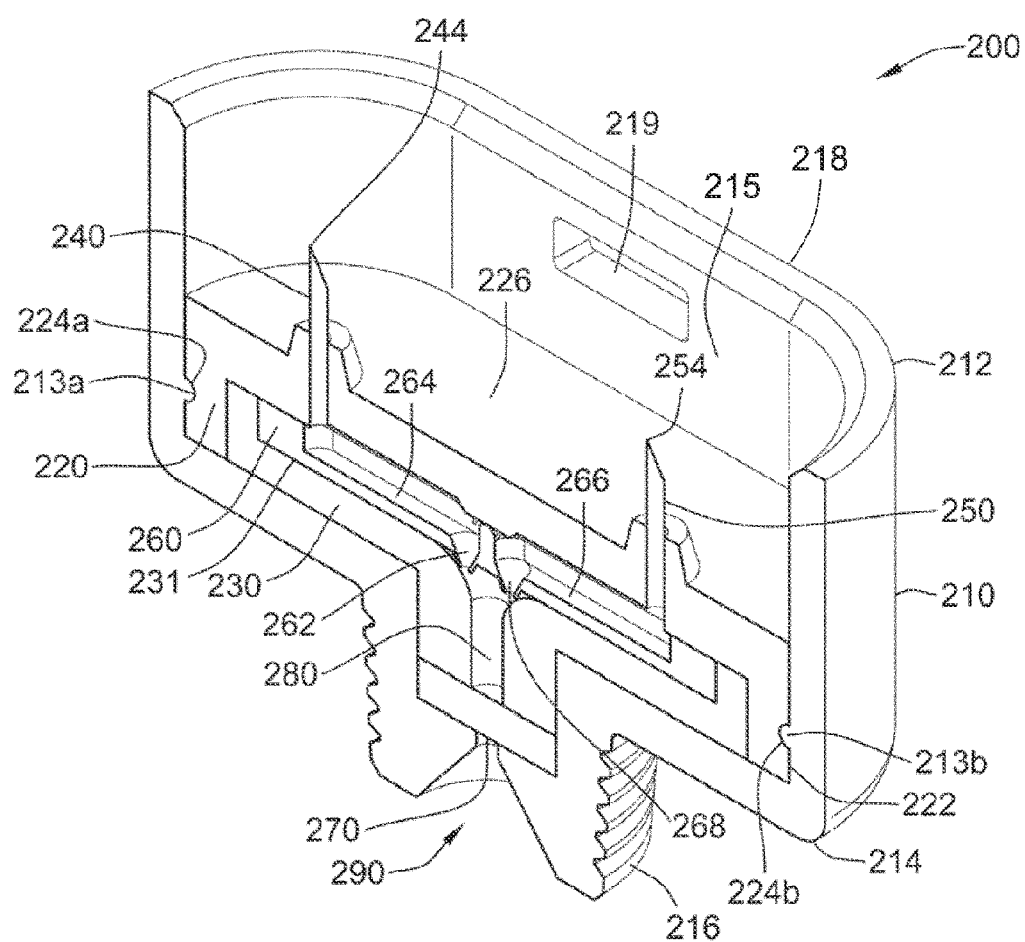
FIG. 9 illustrates a cross-sectional view of the dispense interface illustrated in FIG. 4.
Figure 10:
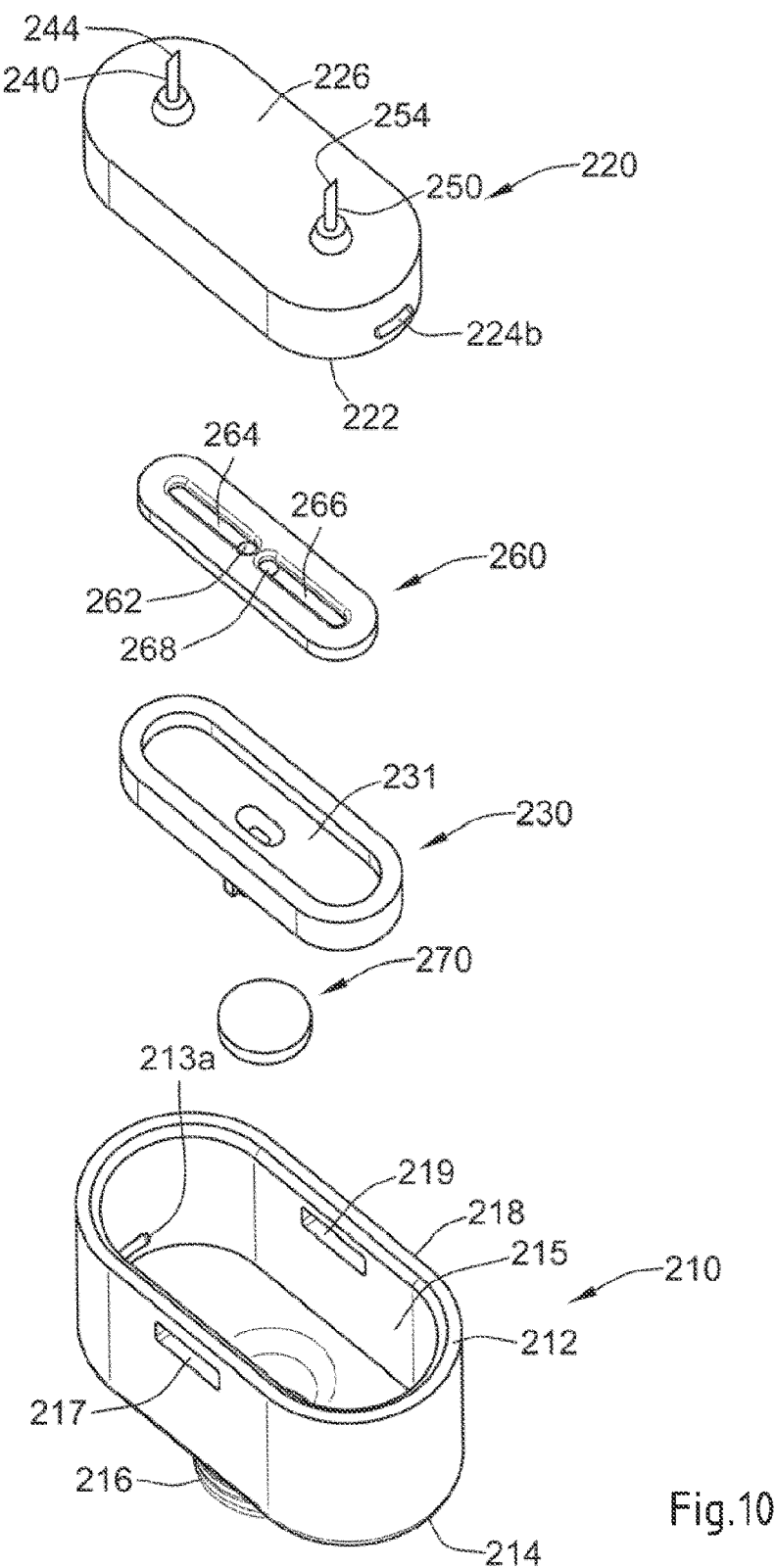
FIG. 10 illustrates an exploded view of the dispense interface illustrated in FIG. 4.

In addition, as can be seen in FIG. 8-10, a proximal surface 226 near the proximal end of the first inner body 220 may be configured with at least a first proximally positioned piercing needle 240 comprising a proximal piercing end portion 244. Similarly, the first inner body 220 is configured with a second proximally positioned piercing needle 250 comprising a proximally piercing end portion 254. Both the first and second needles 240, 250 are rigidly mounted on the proximal surface 226 of the first inner body 220.

Preferably, this dispense interface 200 further comprises a valve arrangement. Such a valve arrangement could be constructed so as to prevent cross contamination of the first and second medicaments contained in the first and second reservoirs, respectively. A preferred valve arrangement may also be configured so as to prevent back flow and cross contamination of the first and second medicaments.

In one preferred system, dispense interface 200 includes a valve arrangement in the form of a valve seal 260. Such a valve seal 260 may be provided within a cavity 231 defined by the second inner body 230, so as to form a holding chamber 280. Preferably, cavity 231 resides along an upper surface of the second inner body 230. This valve seal comprises an upper surface that defines both a first fluid groove 264 and second fluid groove 266. For example, FIG. 9 illustrates the position of the valve seal 260, seated between the first inner body 220 and the second inner body 230. During an injection step, this seal valve 260 helps to prevent the primary medicament in the first pathway from migrating to the secondary medicament in the second pathway, while also preventing the secondary medicament in the second pathway from migrating to the primary medicament in the first pathway. Preferably, this seal valve 260 comprises a first non-return valve 262 and a second non-return valve 268. As such, the first non-return valve 262 prevents fluid transferring along the first fluid pathway 264, for example a groove in the seal valve 260, from returning back into this pathway 264. Similarly, the second non-return valve 268 prevents fluid transferring along the second fluid pathway 266 from returning back into this pathway 266.

Together, the first and second grooves 264, 266 converge towards the non-return valves 262 and 268 respectively, to then provide for an output fluid path or a holding chamber 280. This holding chamber 280 is defined by an inner chamber defined by a distal end of the second inner body both the first and the second non return valves 262, 268 along with a pierceable septum 270. As illustrated, this pierceable septum 270 is positioned between a distal end portion of the second inner body 230 and an inner surface defined by the needle hub of the main outer body 210.

The holding chamber 280 terminates at an outlet port of the interface 200. This outlet port 290 is preferably centrally located in the needle hub of the interface 200 and assists in maintaining the pierceable seal 270 in a stationary position. As such, when a double ended needle assembly is attached to the needle hub of the interface (such as the double ended needle illustrated in FIG. 6), the output fluid path allows both medicaments to be in fluid communication with the attached needle assembly.

The hub interface 200 further comprises a second inner body 230. As can be seen from FIG. 9, this second inner body 230 has an upper surface that defines a recess, and the valve seal 260 is positioned within this recess. Therefore, when the interface 200 is assembled as shown in FIG. 9, the second inner body 230 will be positioned between a distal end of the outer body 210 and the first inner body 220. Together, second inner body 230 and the main outer body hold the septum 270 in place. The distal end of the inner body 230 may also form a cavity or holding chamber that can be configured to be fluid communication with both the first groove 264 and the second groove 266 of the valve seal.

Axially sliding the main outer body 210 over the distal end of the drug delivery device attaches the dispense interface 200 to the multi-use device. In this manner, a fluid communication may be created between the first needle 240 and the second needle 250 with the primary medicament of the first cartridge and the secondary medicament of the second cartridge, respectively.

Figure 11:
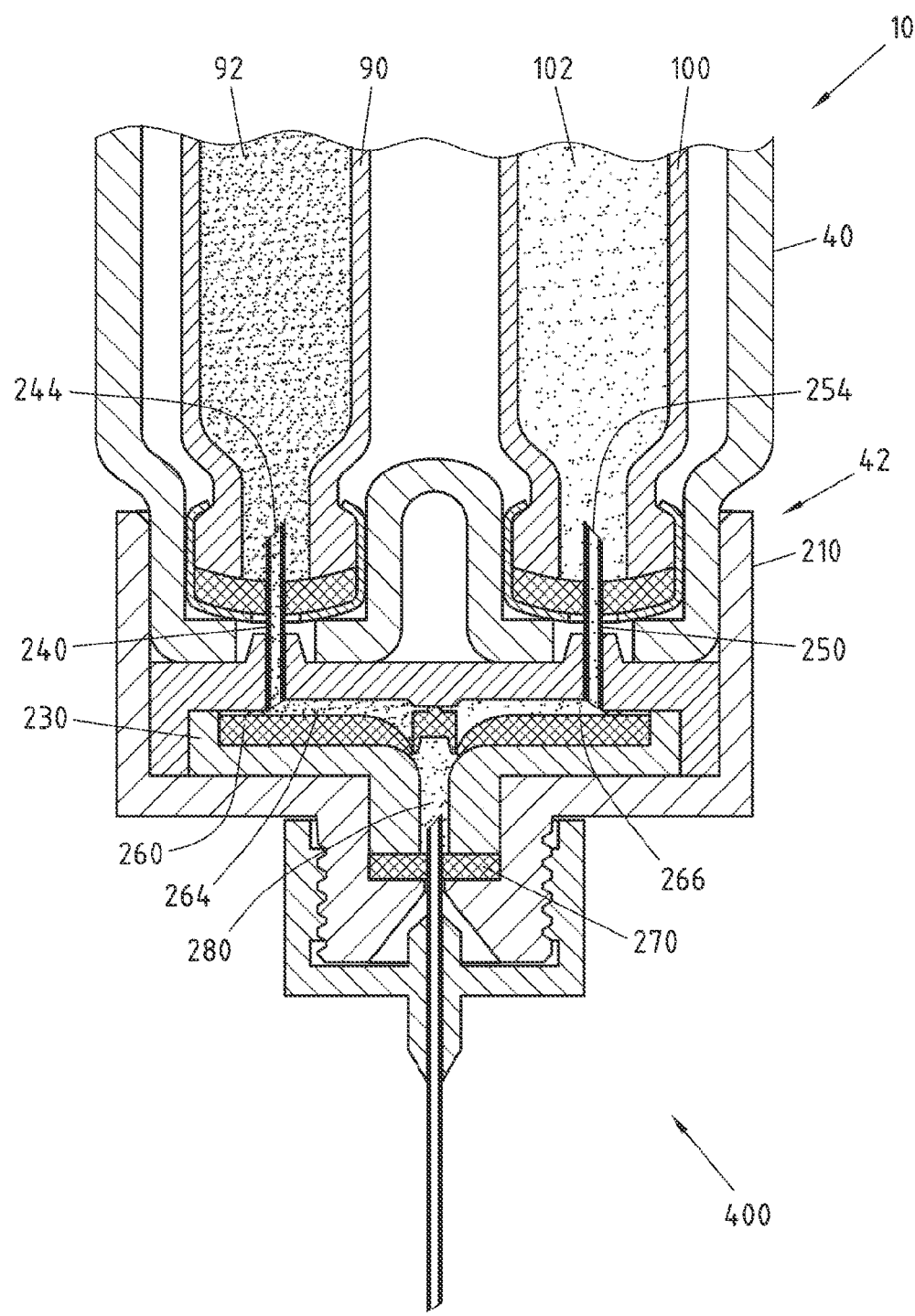
FIG. 11 illustrates a cross-sectional view of the dispense interface and dose dispenser mounted onto a drug delivery device, such as the device illustrated in FIG. 1.

FIG. 11 illustrates the dispense interface 200 after it has been mounted onto the distal end 42 of the cartridge holder 40 of the drug delivery device 10 illustrated in FIG. 1. A double ended needle 400 is also mounted to the distal end of this interface. The cartridge holder 40 is illustrated as having a first cartridge containing a first medicament and a second cartridge containing a second medicament.

When the interface 200 is first mounted over the distal end of the cartridge holder 40, the proximal piercing end 244 of the first piercing needle 240 pierces the septum of the first cartridge 90 and thereby resides in fluid communication with the primary medicament 92 of the first cartridge 90. A distal end of the first piercing needle 240 will also be in fluid communication with a first fluid path groove 264 defined by the valve seal 260.

Similarly, the proximal piercing end 254 of the second piercing needle 250 pierces the septum of the second cartridge 100 and thereby resides in fluid communication with the secondary medicament 102 of the second cartridge 100. A distal end of this second piercing needle 250 will also be in fluid communication with a second fluid path groove 266 defined by the valve seal 260.

FIG. 11 illustrates a preferred arrangement of such a dispense interface 200 that is coupled to a distal end 15 of the main body 14 of drug delivery device 10. Preferably, such a dispense interface 200 is removably coupled to the cartridge holder 40 of the drug delivery device 10.

As illustrated in FIG. 11, the dispense interface 200 is coupled to the distal end of a cartridge housing 40. This cartridge holder 40 is illustrated as containing the first cartridge 90 containing the primary medicament 92 and the second cartridge 100 containing the secondary medicament 102. Once coupled to the cartridge housing 40, the dispense interface 200 essentially provides a mechanism for providing a fluid communication path from the first and second cartridges 90, 100 to the common holding chamber 280. This holding chamber 280 is illustrated as being in fluid communication with a dose dispenser. Here, as illustrated, this dose dispenser comprises the double ended needle assembly 400. As illustrated, the proximal end of the double ended needle assembly is in fluid communication with the chamber 280.

In one preferred arrangement, the dispense interface is configured so that it attaches to the main body in only one orientation, that is it is fitted only one way round. As such as illustrated in FIG. 11, once the dispense interface 200 is attached to the cartridge holder 40, the primary needle 240 can only be used for fluid communication with the primary medicament 92 of the first cartridge 90 and the interface 200 would be prevented from being reattached to the holder 40 so that the primary needle 240 could now be used for fluid communication with the secondary medicament 102 of the second cartridge 100. Such a one way around connecting mechanism may help to reduce potential cross contamination between the two medicaments 92 and 102.

Figure 12:
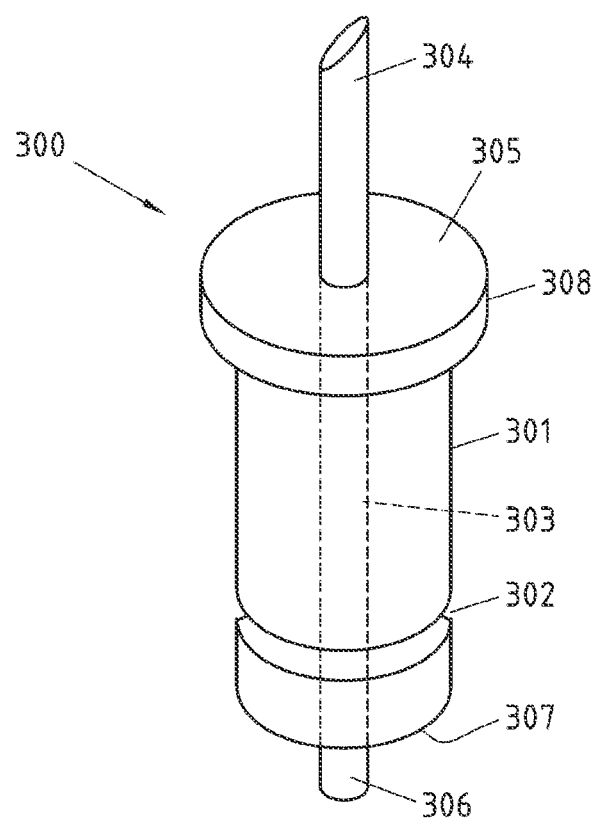
FIG. 12 illustrates a perspective view of a valve piston.

FIG. 12 illustrates a perspective view of a valve piston 300 for an active valve arrangement for the dispense interface 200 illustrated in FIGS. 4 to 10.

As illustrated in FIG. 12, the valve piston 300 is substantially cylindrical and has a lateral surface 301. In the lateral surface 301, a circular recess 302 is arranged. The circular recess 302 may circulate the valve piston partially or entirely. The circular recess may be an engraved channel.

The valve piston 300 is penetrated by a canula 303 arranged along the longitudinal axis of the valve piston 300. A piercing end 304 of the canula 303 protrudes over the top base 305 of the valve piston 300. Another end 306 of the canula 300 protrudes over the bottom base 307 of the valve piston. In particular, the canula 303 corresponds to the piercing needle 240, 250 of the dispense interface 200 illustrated in FIGS. 4 to 10.

Furthermore, the valve piston 300 comprises a projecting rim 308 arranged at the top base 305.

FIG. 13a to d illustrate an embodiment of an active valve arrangement for the dispense interface 200 illustrated in FIGS. 4 to 10. The active valve arrangement comprises the valve piston 300 and a valve body 600. In particular, the valve arrangement replaces the piercing needle 240 and/or 250 of the dispense interface 200 illustrated in FIGS. 4 to 10. The active valve arrangement may for instance also replace the seal valve 260 and/or the first and second non-return valve 262 and 264.

Figure 13A:
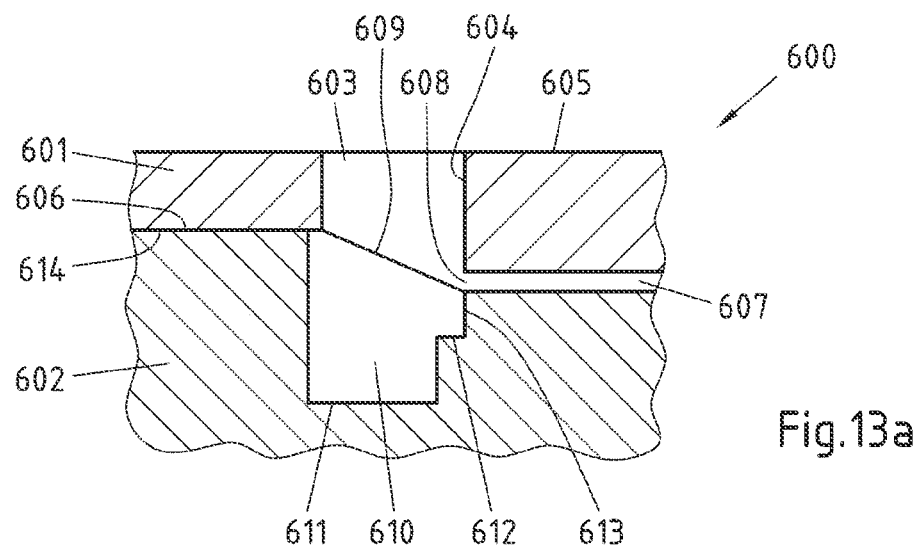
FIGS. 13a-13d illustrate a cross-sectional view of an active valve arrangement in the dispense interface illustrated in FIG. 4-10.

As illustrated in FIG. 13a, the valve body 600 is formed from a cover plate 601 and a base plate 602.

The cover plate 601 comprises a (substantially cylindrical) through opening 603 with a diameter corresponding to the diameter of the valve piston 300 at the lateral surface 301 such that the valve piston 300 may at least partially be received in the opening 603 and tightly encompassed by the lateral surface 604 of the opening 603 of the cover plate 601. The top surface 605 of the cover plate 601 corresponds to the proximal surface 226 of the dispense interface 200.

In the bottom surface 606 of the cover plate 601 a recess 607 is arranged corresponding to the fluid groove 264. The end 608 of the recess ends in the opening 603. The bottom surface 606 of the cover plate is inclined at opening 603 as indicated by the inclination 609.

The base plate 602 comprises a (substantially cylindrical) recess 610 with a diameter larger than the diameter of the valve piston 300 at the lateral surface 301 and the diameter of the opening 603 of the cover plate. At the base 611 of the recess 610 a mechanical stop 612 is arranged. The mechanical stop 612 protrudes over the base 611 of the recess 610 and, for instance lowers the diameter of the recess 610.

The top surface 614 of the base plate 602 is partially inclined at the recess 610 as indicated by the inclination 609. The inclination 609 of the top surface 614 of the base plate 602 corresponds to the inclination 609 of the cover plate 601.

To form the valve body 600, the bottom surface 606 of the cover plate 601 and the top surface 614 of the base plate 602 are bonded, for instance adhesively bonded. Therein, the lateral surface 604 of the opening 603 of the cover plate 601 is flush with the lateral surface 613 of the recess 610 of the base plate 602 at the end 608 of the recess 607. In particular, the lateral surface 604 and the lateral surface 613 form a flush lateral surface in which the end 608 of the recess 607 is arranged. The end 608 forms the outlet port of the valve arrangement.

Opposite to the end 608 of the recess 607 the lateral surface 604 of the opening 603 of the cover plate 601 is not flush with the lateral surface 613 of the recess 610 of the base plate 602 at the end 608 of the recess 607. As illustrated, the recess 610 of the base plate 602 forms a set-back opposite to the end 608.

Figure 13B:
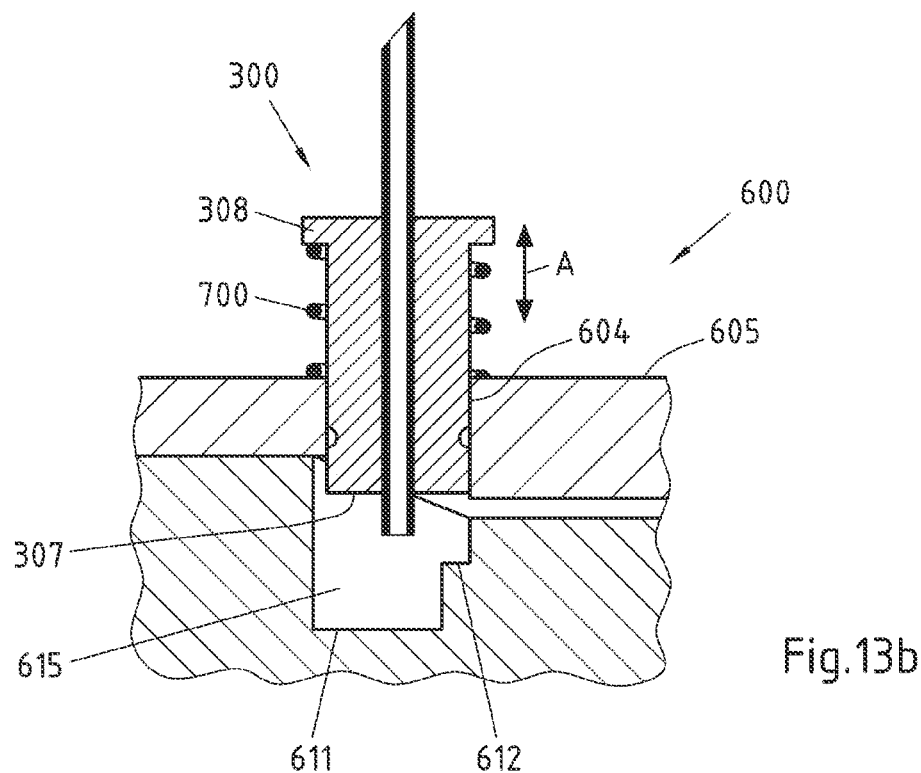
Figure 13C:
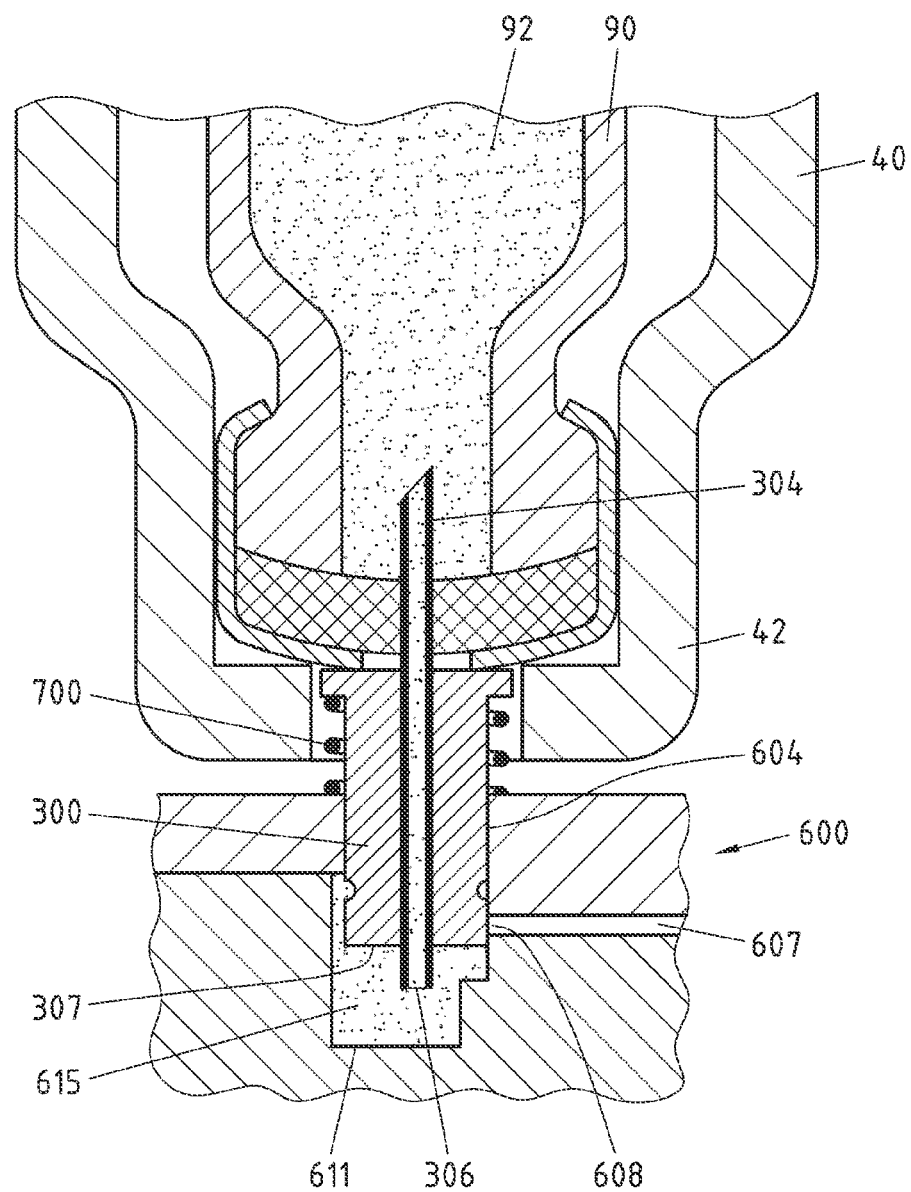
Figure 13D:
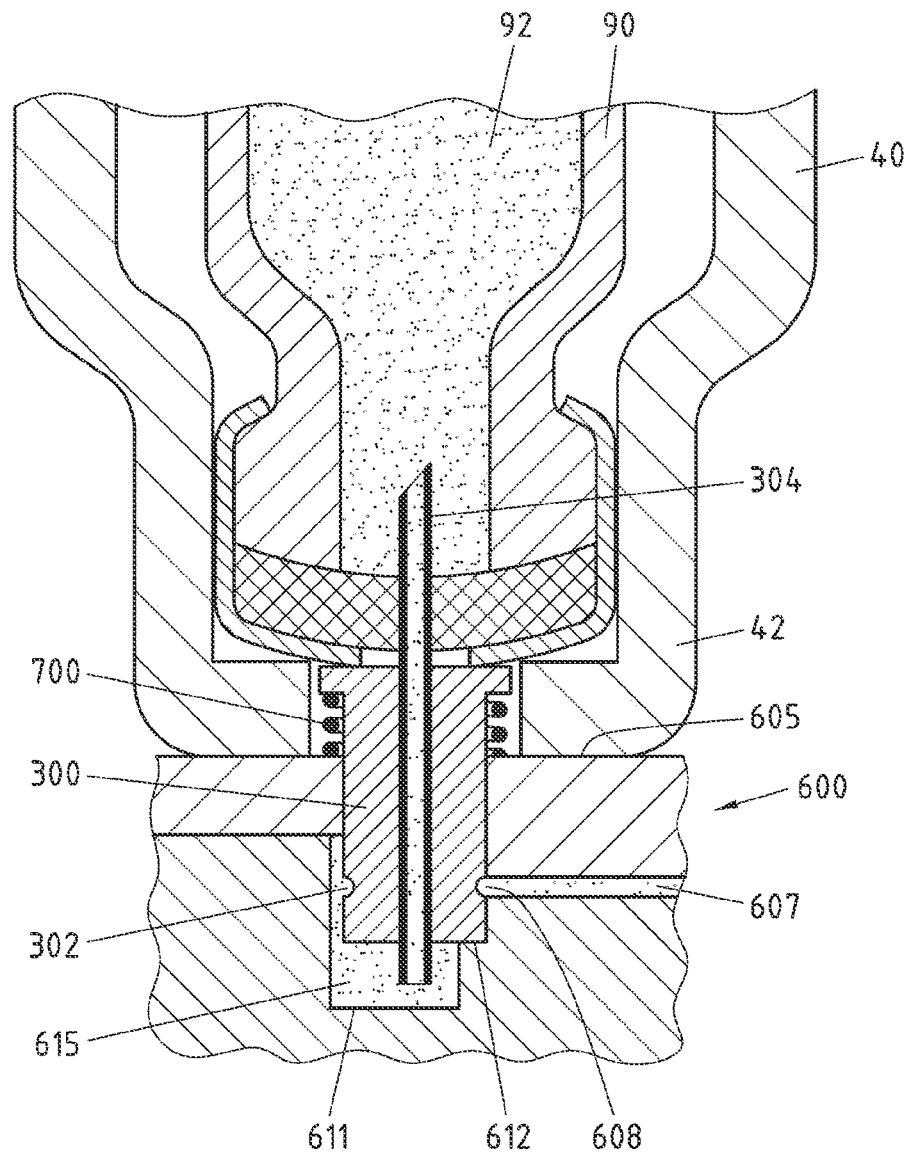

As illustrated in FIG. 13b to d, the valve piston 300 may be longitudinally received in the opening 603 of the valve body 600. Therein, the lateral surface 604 of the opening 603 tightly encompasses the lateral surface 301 of the valve piston 300. The valve piston 300 and the recess 610 of the valve body form a valve cavity 615. The end 306 of the canula 303 ends in the cavity 615 and forms the inlet port of the active valve arrangement. The valve piston 300 is at least partially longitudinally movably in the opening 603 and the recess 610 as indicated by the arrow A.

A spring 700 is arranged between the rim 308 of the valve piston 300 and the top surface 605 of the cover plate 601.

In the initial position of the valve piston 300 in the valve body 600 illustrated in FIG. 13b, the bottom base 307 of the valve piston 300 is longitudinally positioned above the end 608 forming the outlet port of the valve body 600. The valve piston 300 may be received in the initial position in the valve body 600 during assembly, for instance during the assembly of the dispense interface 200. In the initial position of the valve piston 300 in the valve body 600, the spring 700 is relaxed.

As illustrated in FIG. 13c, when the dispense interface 200 comprising the active valve arrangement is first mounted over the distal end 42 of the cartridge holder 40, the piercing end 304 of the canula 303 pierces the septum of the first cartridge 90 and thereby resides in fluid communication with the primary medicament 92 of the first cartridge 90. Furthermore, the canula 303 forms a friction fit with the septum of the first cartridge. The end 306 of the canula 303 will also be in fluid communication with the cavity 615 formed by the valve piston 300 and the recess 610 of the valve body 600. For instance, the septum of the cartridge 90 resides on the top base 305 of the valve piston.

Similarly, another active valve arrangement may provide a connection with the second cartridge 100 (not shown) of the cartridge holder 40.

When the valve piston 300 is connected to the cartridge 90, the valve piston is longitudinally pushed into the valve body such that the lateral surface 301 of the valve piston seals the end 608 forming the outlet port of the active valve arrangement. Thus, in this first longitudinal position of the valve piston 300 in the valve body 600, a fluid flow between the inlet port and the outlet port of the active valve arrangement is disabled, the valve arrangement is closed. The spring 700 secures the valve piston 300 in this first longitudinal position.

As illustrated in FIG. 13d, when a force oriented towards the valve body 600 and the dispense interface 200, respectively, is applied on the cartridge 90, the cartridge 90 is moved in direction of the force and the septum of the cartridge 90 residing on the top base 305 of the valve piston 300 pushes the valve piston 300 into the valve body 600 until the bottom base 307 of the valve piston 300 touches the mechanical stop 612. In this second longitudinal position of the valve piston 300 in the valve body 600, when the bottom base 307 of the valve piston 300 resides on the mechanical stop 612, the recess 302 is aligned with the end 608 forming the outlet port of the active valve arrangement such that the recess 302 provides fluid communication between the end 608 and the valve cavity 615. Thus, in this second longitudinal position of the valve piston 300 in the valve body 600, a fluid flow between the inlet port and the outlet port of the active valve arrangement is enabled, the valve arrangement is open.

Furthermore, in the second longitudinal position of the valve piston 300 in the valve body 600, the spring 700 is compressed and causes an elastic counterforce. Thus, when the force applied on the cartridge 90 is released, the spring 700 relaxes and thereby moves the valve piston 300 and the cartridge 90 to the first longitudinal position illustrated in FIG. 13c.

To start the injection of the medicament 92 contained in cartridge 90, a force oriented towards the dispense interface 200 and the valve body 600, respectively, is applied on a bung arranged in the cartridge and, due to the friction between the bung and the cartridge 90, this force is firstly (at least partially) translated into a movement of the cartridge 90 and the valve piston 300. In particular, the valve piston 300 may be moved from the first longitudinal position in the valve body 600 to the second longitudinal position in the valve body 600. When the valve piston 300 is in the second longitudinal position in the valve body 600, the mechanical stop 612 prevents a further movement of the valve piston 300 and the cartridge 90, and then the bung is moved within the cartridge in direction of the force such that a pressure is build up in the cartridge 90.

As described above, in the second position of the valve piston 300 in the valve body 600, the valve arrangement is open and, due to the build up pressure in the cartridge, a flow of the medicament 92 from the cartridge 90 via the canula 303, the cavity 615, the recess 302 and the recess 607 to the outlet 290 (not shown) of the dispense interface 200 may be initiated.

To prevent a backflow of the medicament 92 after the injection, the spring 700 moves the valve piston 300 from the second longitudinal position to the first longitudinal position, when the force applied on the bung arranged in the cartridge 90 is released. To deliver the next dose, the bung again moves the cartridge 90 and the valve piston 300 in the second longitudinal position, when the drug delivery is initiated.

The present invention provides an active valve arrangement formed from at least two pieces, the valve body 600 and the valve piston 300, wherein the valve piston 300 may be received in the valve body 600, when the valve arrangement is to be connected to a fluid reservoir. This is inter-alia advantageous in order to provide a simply mountable valve for a valve arrangement of the dispense interface 200. Furthermore, the cover plate 601 and the base plate 602 also allow a simple assembly of the valve body.

Furthermore, the present invention provides an active valve arrangement, wherein the valve arrangement is actively opened and closed depending on a movement of the cartridge 90 and/or a force applied on a bung arranged in the cartridge 90. This is inter alia advantageous in order to provide a valve without an opening pressure threshold, minimal resistance to flow when open and an effective seal against back pressure.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(02)25, Asp28] Exendin-4(1-39),
des Pro36 [Met(O)14 Trp(02)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39), des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2) 25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2) 25, Asp28] Exendin-4(1-39)-(Lys)6-NH2;
or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The invention claimed is:

1. A valve arrangement, comprising:
   a valve body comprising a fluidic channel having an outlet port; and
   a valve piston, the valve piston comprising a through opening connecting an end with a piercing end that provides fluid communication between the piercing end and the outlet port to allow fluid to pass through the valve piston, and the valve piston comprising an outer lateral surface having a circular recess formed therein,
   wherein the valve piston is moveable within the valve body between a first longitudinal position and a second longitudinal position,
   wherein the circular recess of the valve piston is not in fluid communication with the outlet port, to disable a fluid flow between the outlet port and the end via the circular recess, when the valve piston is in the first longitudinal position within the valve body, and
   wherein the circular recess of the valve piston is in fluid communication with the outlet port, to enable the fluid flow between the outlet port and the end, when the valve piston is in the second longitudinal position within the valve body.

2. The valve arrangement according to claim 1, wherein the valve body comprises an opening configured to at least partially receive the valve piston and to form a cavity with the valve piston.

3. The valve arrangement according to claim 2, wherein the valve body is formed from at least a cover part and a base part, the cover part configured to form an inlet of the opening and the base part configured to form the cavity with the valve piston.

4. The valve arrangement according to claim 2, wherein the cavity is variable depending on the positions of the valve piston.

5. The valve arrangement according to claim 2, wherein the end ends in the cavity, and wherein the outlet port ends in the cavity, when the valve piston is in the second position.

6. The valve arrangement according to claim 1, wherein the outer lateral surface of the valve piston is configured to seal the outlet port in the first position and to unseal the outlet port in the second position.

7. The valve arrangement according to claim 1, wherein the valve piston is substantially cylindrical.

8. The valve arrangement according to claim 1, wherein the valve piston is spring-loaded.

9. The valve arrangement according to claim 1, wherein the channel that extends axially within the valve piston is formed from a cannula, wherein one end of the cannula is configured to pierce a septum of a fluid reservoir such that the end resides in fluid communication with the fluid reservoir.

10. The valve arrangement as claimed in claim 1, wherein the valve arrangement is part of a medical device configured to eject a medicament or is part of a dispense interface attachable to a medical device configured to eject a medicament.

11. A method for enabling a fluid flow in an apparatus, wherein the apparatus comprises a valve arrangement having a valve body, the valve body comprising a outlet port and a valve piston, the valve piston comprising an end in fluid communication with a channel that extends axially within the valve piston, and the valve piston comprising an outer lateral surface having a circular recess formed therein, wherein the valve piston is moveable within the valve body between a first longitudinal position and a second longitudinal position, wherein the circular recess of the valve piston is not in fluid communication with the outlet port, to disable a fluid flow between the outlet port and the second port via the circular recess, when the valve piston is in the first longitudinal position within the valve body, wherein the circular recess of the valve piston is in fluid communication with the outlet port, to enable the fluid flow between the outlet port and the end, when the valve piston is in the second longitudinal position within the valve body, and wherein the apparatus is a medical device configured to eject a medicament or a dispense interface attachable to a medical device configured to eject a medicament, the method comprising:
   moving a fluid reservoir connected to the end relatively to the apparatus; and
   enabling a fluid flow between the outlet port and the end, wherein moving the fluid reservoir causes the valve piston to move from the first position to the second position.

12. The method according to claim 11, wherein the valve piston is spring-loaded such that moving the fluid reservoir relatively to the apparatus is against a spring-load and causes an elastic counterforce.

* * * * *